United States Patent
Eberhard et al.

(10) Patent No.: US 7,142,633 B2
(45) Date of Patent: Nov. 28, 2006

(54) ENHANCED X-RAY IMAGING SYSTEM AND METHOD

(75) Inventors: Jeffrey Wayne Eberhard, Albany, NY (US); Bernhard Erich Hermann Claus, Niskayuna, NY (US); Cynthia Landberg, Clifton Park, NY (US)

(73) Assignee: General Electric Company, Niskayuna, NY (US)

( * ) Notice: Subject to any disclaimer, the term of this patent is extended or adjusted under 35 U.S.C. 154(b) by 89 days.

(21) Appl. No.: 10/813,759

(22) Filed: Mar. 31, 2004

(65) Prior Publication Data

US 2005/0226375 A1    Oct. 13, 2005

(51) Int. Cl.
G01N 23/04    (2006.01)

(52) U.S. Cl. .................................. 378/62; 378/901

(58) Field of Classification Search ................ 378/4, 378/21–27, 37, 62, 901
See application file for complete search history.

(56) References Cited

U.S. PATENT DOCUMENTS

| | | | |
|---|---|---|---|
| 4,903,204 A | 2/1990 | Dobbins, III | 382/255 |
| 5,187,659 A | 2/1993 | Eberhard et al. | 378/9 |
| 5,872,828 A | 2/1999 | Nikalson et al. | 378/23 |
| 6,574,304 B1* | 6/2003 | Hsieh et al. | 378/62 |
| 6,707,878 B1* | 3/2004 | Claus et al. | 378/22 |
| 2002/0085681 A1* | 7/2002 | Jensen | 378/197 |
| 2003/0194121 A1* | 10/2003 | Eberhard et al. | 382/132 |

* cited by examiner

Primary Examiner—Courtney Thomas
(74) Attorney, Agent, or Firm—Fletcher Yoder

(57) ABSTRACT

Techniques are provided for generating three-dimensional images, such as may be used in mammography. In accordance with these techniques, projection images of an object of interest are acquired from different locations, such as by moving an X-ray source along an arbitrary imaging trajectory between emissions or by individually activating different X-ray sources located at different locations relative to the object of interest. The projection images may be reconstructed to generate a three-dimensional dataset representative of the object from which one or more volumes may be selected for visualization and display. Additional processing steps may occur throughout the image chain, such as for pre-processing the projection images or post-processing the three-dimensional dataset.

25 Claims, 8 Drawing Sheets

ENHANCED X-RAY IMAGING SYSTEM AND METHOD

BACKGROUND OF THE INVENTION

The present invention relates generally to the field of non-invasive imaging and more specifically to the field of medical imaging. In particular, the present invention relates to the generation of three-dimensional image data, such as in a mammography context.

Mammography is an imaging technique by which a breast may be non-invasively examined or screened to detect abnormalities, such as lumps, fibroids, lesions, calcifications, and so forth. Typically mammography employs radiographic techniques to generate images representative of the breast tissue. In particular, the breast is typically compressed to near uniform thickness and X-rays are passed through the compressed breast. The X-rays are attenuated by the breast tissue, with abnormalities presumably giving rise to discernible attenuation differences or structural distortions, and impact a detector. The detector, in turn generates responsive signals which may be processed to generate an image representing the breast tissue, which may be examined for visible indications of abnormalities.

While mammography is a useful tool for breast examination and screening, the images acquired by mammography may not provide as much information or detail as desired. In particular, the single view X-ray images associated with mammography may be difficult to interpret since all of the anatomic structure of the imaged breast is superimposed in the image. In other words, the mammogram provides only a two-dimensional representation of the three-dimensional breast, meaning overlying and underlying structure may be superimposed on in a region of clinical interest. As a result, the sensitivity rate for X-ray mammography is relatively low (typically between 70% and 80%) and the false positive rate is undesirably high (between 70% and 90% of biopsies are normal). A technique for providing more information to a radiologist in a mammography context may, therefore, be desirable.

BRIEF DESCRIPTION OF THE INVENTION

The present invention provides for the acquisition of two or more mammographic images at different orientations or positions relative to the imaged breast. The acquired projection images may then be reconstructed to generate a three-dimensional dataset. Various processing steps, such as filtration, artifact correction, normalization, and so forth, may be performed on the image data, prior to and/or subsequent to reconstruction of the three-dimensional dataset. Selected volumes of the three-dimensional dataset may be visualized and displayed, providing three-dimensional context and data to a reviewing radiologist. If desired, the visualized and displayed image data may incorporate or be presented with other image data, such as previous tomosynthesis mammography screenings or image data acquired by other modalities. Furthermore, the images, such as the projection images and/or the three-dimensional dataset, may also be examined by CAD techniques at any point in the imaging process.

In accordance with one aspect of the present technique, a method is provided for generating a three-dimensional dataset. In accordance with the method, a plurality of projection images are acquired from different locations on an arbitrary source path. The plurality of projection images are reconstructed to form a three-dimensional dataset. Systems and computer programs that afford functionality of the type defined by these methods are also provided by the present technique.

BRIEF DESCRIPTION OF THE DRAWINGS

The foregoing and other advantages and features of the invention will become apparent upon reading the following detailed description and upon reference to the drawings in which.

DETAILED DESCRIPTION OF SPECIFIC EMBODIMENTS

The present technique is generally directed to the use of tomosynthesis imaging techniques to generate more useful images, such as for mammography or other medical or non-medical applications. In general, tomosynthesis imaging techniques allow for the reconstruction of a volumetric data set from an incomplete set of projection images, i.e., insufficient projection images to fill Radon space. In the context of the present technique, multiple projection images may be acquired at different orientations relative to an imaged object, such as a breast. The projection images may then be processed to generate a volumetric dataset, which may be used for the visualization and display of selected volumes of image data. In a mammography context the tomosynthesis mammograms may provide information, such as three-dimensional context, that is unavailable in standard mammography exams. As will be appreciated by those of ordinary skill in the art, the present techniques may also be applied in other medical and non-medical contexts, such as for passenger, package, and/or baggage screening, to provide useful three-dimensional data and context. To facilitate explanation of the present techniques, however, a mammography implementation will be generally discussed herein, though it is to be understood that other non-medical and medical implementations are also within the scope of the present techniques.

Figure 1:
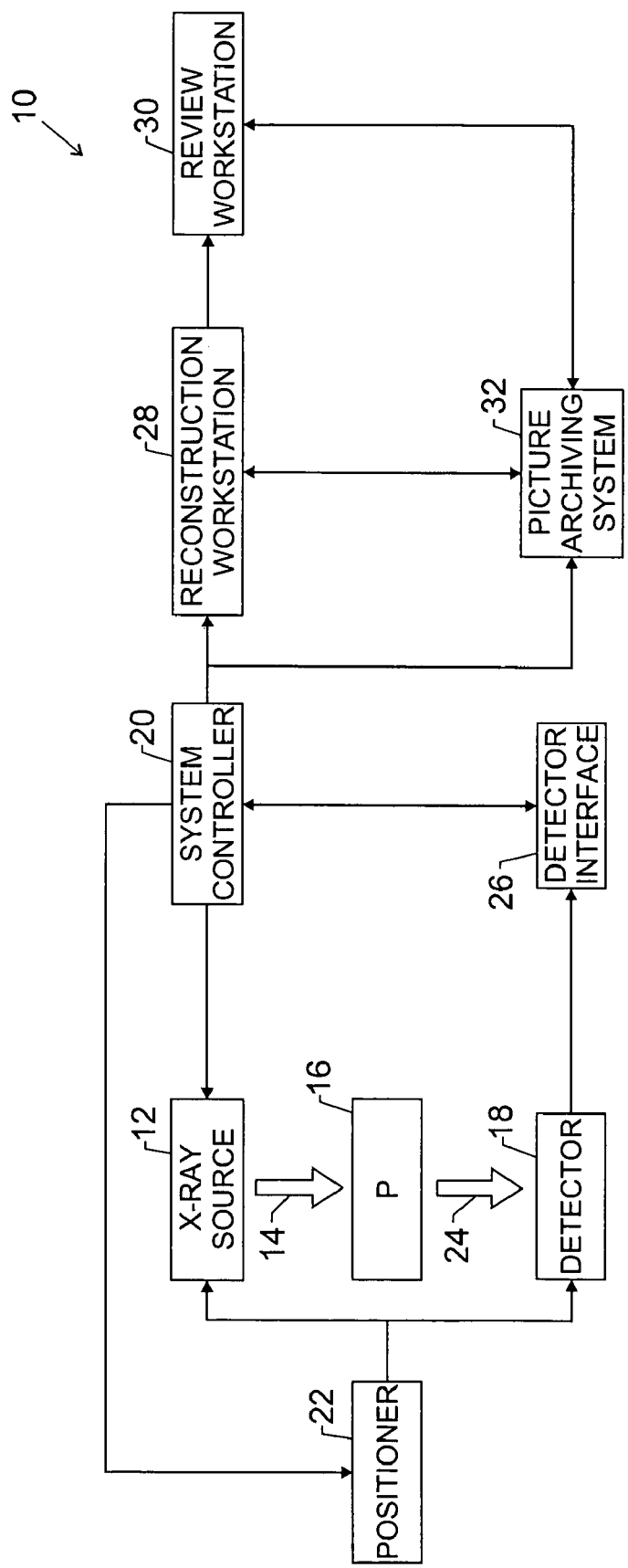
FIG. 1 is a block diagram depicting some of the components of an exemplary tomosynthesis mammography system, in accordance with the present technique.

An exemplary X-ray imaging system 10 for use in conjunction with the present technique is depicted in FIG. 1 as a block diagram. As depicted the X-ray imaging system 10 may include an X-ray source 12, which may comprise one or more emission points or producers of X-ray radiation 14. For example, The X-ray source 12 may comprise an X-ray tube and generator configured to generate a beam of X-rays 14 when activated. In addition, the X-ray source 12 may be movable in one, two or three dimensions, either by manual or by automated means, such that the position of an emission point may be changed with respect to a patient 16 and/or a detector 18. As noted above, the X-ray source 12 may include multiple X-ray producing components, such as X-ray tubes, or X-ray emission points, such as field emitters of a solid-state source, disposed at the desired orientations about the breast. Where the X-ray source 12 includes multiple emission points, the individual activation of the emission points in a desired sequence may functionally equate to the physically movement of an individual emission point relative to the imaged anatomy. Therefore, those of ordinary skill in the art will appreciate that, as discussed herein, moving an X-ray source 12 and/or emission point may be accomplished by the physical movement of an X-ray emitter, by activating two or more such emitters in a sequence that equates to such physical movement, or by some combination of these approaches.

Activation of the X-ray source 12 may be controlled by a system controller 20 which may control the activation and operation, including collimation, of the X-ray source 12. In particular, the system controller 20 may be configured to provide power and timing signals to the X-ray source 12. In addition, the system controller 20 may control the motion of the X-ray source 12 and/or the detector 18 in accordance with a pre-configured or operator selected imaging trajectory, such as an imaging trajectory for use in mammography. The system controller 20 may also execute various signal processing and filtration functions, such as for initial adjustment of dynamic ranges, interleaving of digital image data, and so forth. In general, system controller 20 commands operation of the imaging system 10 to execute examination protocols and to acquire the resulting data.

If the X-ray source 12 and the detector 18 are configured to move, the source 12 and detector 18 may move independent of one another or may move in synchrony, such as by automatically positioning the detector 18 based on the movement of the source 12. In particular, the system controller 24 may control the operation of a positioner 22 that provides for the physical motion required by the X-ray source 12 and/or the detector 18. Therefore, by means of the positioner 22, the system controller 20 may facilitate the acquisition of radiographic projections at various angles through the patient 16. The positioner 22 may move the X-ray source 12 and/or the detector 18 via tracks, ballscrews, gears, belts, piezoelectrics, and so forth. For example, the X-ray source 12 may be located at the end of a mechanical support, such as a rotating arm or otherwise adjustable support, which may be moved by the positioner 22. Similarly, the X-ray source 12 may move along tracks or by means of other mechanical supports which allow movement along a generalized or arbitrary trajectory. While an X-ray tube is one example of an X-ray source 12 which may be moved in this manner, other types of X-ray sources 12, such as some or all of the emitters of a solid state X-ray source, may also be mechanically moved along a generalized or arbitrary trajectory. In general, the technique used for moving the source 12 and/or detector 18 will be selected to minimize or reduce detrimental effects on image quality, such as from vibration, electromagnetic interference, and so forth.

The X-rays 14 emitted by the X-ray source 12 may pass through the anatomy of the patient 16, such as a breast in an X-ray mammography system, which may attenuate the X-ray beam 14, such as by absorption, scatter, and so forth. The attenuated X-rays 24 may then impact the detector 18. The detector 18 is typically a digital X-ray detector, such as one or more amorphous silicon flat-panels with a CsI scintillator. In general, the detector 18 or panels comprising the detector 18 are comprised of an array or detector elements that each generate responsive signals of varying strength based upon the strength of the attenuated X-rays 24 incident upon the respective element. While a flat-panel detector may be employed, non-planar and/or multi-panel detectors may also be employed in conjunction with the present technique. In the case of multi-panel detectors, the panels may be arranged in different orientations such as to optimize geometric coverage of the imaged region, and/or signal level, etc. Furthermore, the different panels of a multi-panel detector may be moveable, either in concert or separately. The type of detector 18 selected may be based upon geometrical and/or patient positioning constraints or upon a desire to minimize missing data by facilitating acquisition of image data near the edges of the imaged object, such as at the junction of the breast and chest wall in mammography.

The detector 18 may be interfaced to the X-ray imaging system 10 through a detector interface 26, such as a PC DAS (Personal Computer-Data Acquisition System) or an IDC (Integrated Detector Controller). The detector interface 26 may control or coordinate the readout of the signals generated by the respective detector elements of the detector 18 based on instructions from the system controller 20. For example, the detector interface 26 may acquire sampled analog signals from the detector 18 and may convert such signals to digital form for subsequent processing. The detector interface 26 may communicate the raw or converted signals to the system controller 20 for processing or transmission to downstream processor-based systems. Though the system controller 20, and the respective user interface, is depicted separately from the detector interface 26 in FIG. 1, the system controller 20 and detector interface 26 may both be resident on a suitable computer configured specifically for these functions, such as a PC-DAS. Alternately, the system controller 20, along with a suitable user interface, may be resident on a suitable computer separate from the computer performing the detector interface functions.

The acquired signals may be sent to a reconstruction workstation 28, if present, for processing and reconstruction. The relative positions of the source 12 and the detector 18 to one another and/or to the patient 16 at a point in time may be tracked or determined by various means, such as by positioner feedback, spatial sensors, or from the acquired images, and utilized during the reconstruction process. For example, anatomical markers, and/or other markers that are visible in the acquired images may be used to determine the imaging geometry. Furthermore, a combination of different techniques may be employed to determine the imaging geometry. The image data reconstructed at the reconstruction workstation 28 may be sent to a review workstation 30 for analysis and review, such as by a radiologist. As depicted, the reconstruction workstation 28 and review workstation 30 may be separate systems. Alternately, the reconstruction and review functions may be resident on a single workstation. In addition, a data archiving system, such as a picture archiving system (PACS) 32, may be present to acquire and store raw image data, such as from the system controller 20, reconstructed image data, such as from the reconstruction workstation 28, and/or processed or annotated image data, such as from the review workstation 30.

Similarly, the reconstruction workstation 28 and/or review workstation 30 may acquire appropriate image data from the picture archiving system 32 for further or subsequent processing. As one of ordinary skill in the art will appreciate, the data archiving system may be local or remote to the other constituents of the imaging system 10 and may store data with or without compression. Patient records may be stored in conjunction with image data on the data archiving system.

User interaction with the various computers and controllers comprising the imaging system 10 may include various input devices configured to allow an operator to specify or input different operational parameters and/or options. Operator input may be provided by various techniques, including choosing options from a menu or selectable interface, setting parameters within allowable ranges, or updating/modifying current parameters. The operator input may be provided to the respective computer or controller via a keyboard, a touch-sensitive screen, a mouse or similar point-and-click interface, and/or a speech recognition interface, or other suitable input device. Similarly various output devices may be present which allow the operator to review images, measurements, and/or parameters generated by the imaging system 10. Operator feedback may be visual (such as via a screen, monitor, or display), audible (such as via one or more speakers over which a voice or artificial speech message is played), or tactile (such as via a pressure feedback device or virtual reality glove).

The various computers and controllers comprising the imaging system 10 may communicate with one another, such as via a local, wide or storage area network, or even via the internet. Conventional, i.e., wire, connections can be used, as can optical and wireless connections. For example, a review workstation 30 may be situated at a site remote from the actual image acquisition site, allowing an expert radiologist to perform remote analysis of the acquired image data, such as in the case of telemammography. When such remote sites are present, high-speed connections, such as over Internet2, may be employed to facilitate the timely transfer of large image datasets, such as datasets characteristic of three-dimensional imaging. As one of ordinary skill in the art will appreciate, the various computers, controllers, and workstations discussed herein may, in practice, consist of any suitably configured processor-based system that may be configured to perform the desired functions, such as image acquisition and/or manipulation.

In addition, the various processor-based systems described with regard to imaging system 10 may comprise or communicate with various types of memory circuitry that can store images, executable routines, or other data. It should be understood that any type of computer accessible memory device capable of storing the desired amount of data and/or code may be utilized by such an exemplary system 10. Moreover, the memory circuitry may comprise one or more memory devices, such as magnetic or optical devices, of similar or different types, which may be local and/or remote to the system 10. The memory circuitry may store data, processing parameters, and/or computer programs comprising one or more routines for performing the processes described herein.

As one of ordinary skill in the art will appreciate, the various components of the imaging system 10 may be routinely calibrated to maintain the desired physical and/or radiological characteristics. For example, with regard to the X-ray source 12 and the detector 18 discussed above, properties which may be calibrated include detector position, X-ray tube position, X-ray tube and detector parameters (pixel-by-pixel detector sensitivity, dark current, non-functioning pixels, and so forth). Similarly, display and print devices may be calibrated to provide consistent visual data in terms of intensity, dynamic range, and so forth.

Calibration of the desired component or components may be accomplished using a specified calibration acquisition routine, such as in conjunction with specific calibration phantoms or in the context of a patient exam. Examples of possible calibration phantoms include material decomposition calibration phantoms or suitable spatial arrangements of spherical BB's or other geometric structures for geometry calibration. Alternatively, calibrations performed in the context of a patient exam may be performed based on markers extracted from the imaged anatomy or on other properties of the imaged object. In addition, the calibration routine may utilize data acquired from one or more additional sensors, such as one or more positional sensors or a reference detector providing data for image normalization. These system calibrations may, be performed periodically, such as once per week, or in conjunction with each data acquisition. Any component of the imaging system 10 may be calibrated using one or more of the strategies that were discussed above, or using other strategies known in the art.

The exemplary imaging system 10 as described with regard to FIG. 1 may be used to generate image data that may be reconstructed and combined to reveal internal features of the patient 16, such as in the context of mammography. For example, some or all of the exemplary imaging system 10 may be used in the implementation of the present technique, such as via the steps discussed below with regard to FIG. 2. As will be appreciated by those of ordinary skill in the art, some of the steps depicted in the exemplary image chain of FIG. 2 may be optional and/or may be performed in a different order than depicted.

Patient Positioning

Figure 2:
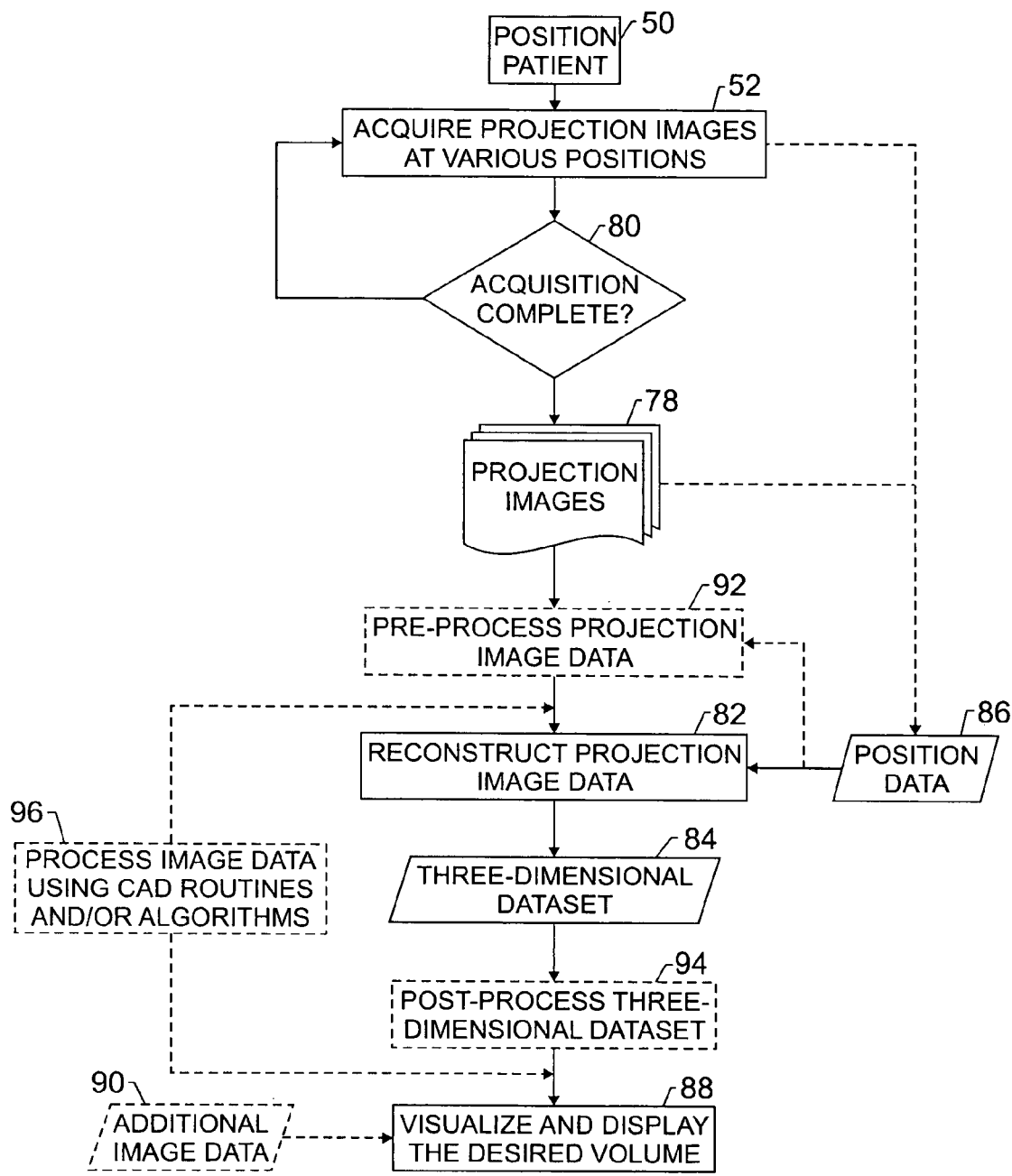
FIG. 2 is a flow chart depicting some of the steps in an exemplary tomosynthesis mammography image chain, in accordance with the present technique.
Figure 3:
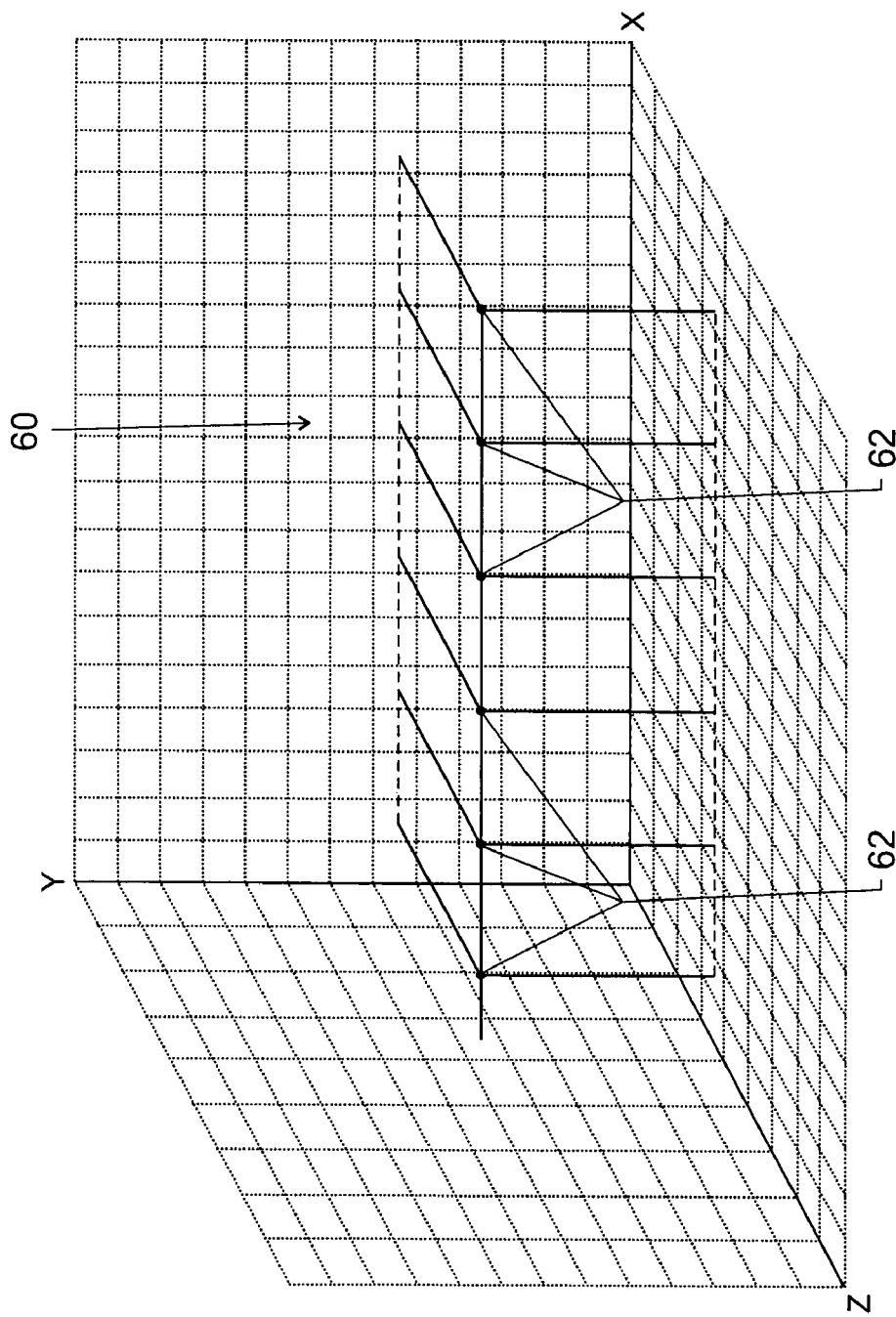
FIG. 3 depicts source positions generally along a linear imaging trajectory, in accordance with the present technique.

As depicted at step 50 of FIG. 2, the patient 16 may be positioned relative the source 12 and the detector 18 such that the X-rays emitted from the source 12 pass through the breast being imaged before impacting elements on the detector 18. Depending on the configuration of the source 12 and the detector 18, the patient may be standing, sitting or lying prone during the imaging process. Typically, positioning of the patient at step 50 results in the breast to be imaged remaining or being held stationary. For example, the breast may be compressed, immobilized, and/or pendant through an aperture in a table. If the breast to be imaged is compressed, standard compression devices may be employed, such as flat, inflexible plates, or alternative compression devices may be employed, such as flexible and/or non-planar compression surfaces. Feedback from the positioning process (e.g., compression force, compressed thickness, etc.) may be provided to other system components so as to optimize image acquisition, image reconstruction, and/or other imaging processes. Anatomical and/or fiducial markers may be employed in conjunction with the positioning step 50 to provide information about position, motion, and or deformation of the imaged anatomy during the acquisition of image data. In particular, use of anatomical and/or fiducial markers may be desirable if the breast is not immobilized or compressed during the imaging process. If desired, X-ray opaque contrast agents may be administered to the patient to enhance information content of the images.

Image Acquisition: Source

The acquisition of projection images is depicted at step 52. Generally, to obtain three-dimensional information, projection images are acquired at different positions relative to the breast and/or detector 22. The plurality of positions from which X-ray exposures occur, regardless of the number of tubes or emitters employed or their motion, constitute an imaging trajectory describing the acquisition of projection images relative to the breast of the patient 16 over time.

For example, if the X-ray source 12 comprises a movable X-ray tube, the X-ray tube may be moved in a one, two or three-dimensional source path relative to the imaged breast. X-rays may be emitted from the X-ray tube as it pauses at specified positions on the source path or as it moves through the specified positions. In circumstances where the emitting X-ray source 12 moves during X-ray emission (such as when a fast acquisition with a minimum of vibration is desired) the amount of motion during each emission period may be limited to reduce motion blurring.

In implementations such as this where the X-ray source 12 (or sources) move, the source path may be arbitrary. One characteristic of such an arbitrary source path, as discussed herein, is that an arbitrary source path may trace virtually any geometric shape (such as linear, arcuate, ovoid, elliptical, hyperbolic, sinusoidal, and so forth) or no specific geometric shape (such as a composite or random path). In addition, an arbitrary source path may have virtually any orientation with respect to the patient, and is not limited, such as by hardware constraints, to a specified path. In particular, an arbitrary source path is not confined to move within a specified plane or at a fixed distance from some fulcrum point. In other words, an arbitrary source path allows for movement of an X-ray emitter or tube in an unfixed manner relative to the patient 18 and/or the detector 22. An arbitrary source path, therefore, may be adjusted or adapted based on circumstance, such as in response to patient specific factors.

Alternatively, the X-ray source 12 may comprise multiple X-ray tubes or a solid-state source with multiple emitters. In such an implementation, the tubes or emitters may be activated one at a time to allow the acquisition of projection images at different positions relative to the breast being imaged. Similarly, a combination of multiple X-ray tubes or emitters, some or all of which may be movable during image acquisition, may be employed to acquire projection images at different positions relative to the breast. In such implementations, the position and timing of X-ray emissions, regardless of the number of tubes or emitters employed or their motion, describe the imaging trajectory.

Examples of imaging trajectories, which may generated by one or more movable X-ray tubes or emitters or by two or more spatially fixed X-ray tubes or emitters, are depicted in FIGS. 3–7. For example, referring to FIG. 3, a linear imaging trajectory 60 is depicted in which X-ray emissions occur at emission points 62 at different times, such as by activating stationary, linearly displaced X-ray tubes and/or emitters one at a time. Alternatively, an X-ray tube or emitter may be moved along a source path conforming to the linear imaging trajectory 60 and activated in accordance with the respective emission points 62. As noted previously, the emission of X-rays may occur as the X-ray tube is stopped and activated at each emission point 62 or as the X-ray tube is activated for a time interval as each emission point 62 is approached or crossed by the X-ray tube. In addition, for imaging trajectories in which a moving X-ray tube is employed, the X-ray tube may also undergo an angulation motion, depending on its current position with respect to the detector and/or the imaged anatomy. In particular, the X-ray tube may be angularly adjusted as the source path is traversed to keep the beam of X-rays pointed generally toward the center of the detector 18.

Similarly, an adjustable collimator may be associated with the X-ray source 12 and may be used to keep the X-ray beam centered on the active area of the detector 18, thereby limiting the exposure of surrounding tissues, and the nearby environment, to the X-rays. In one embodiment, the collimator may be used to further limit the emitted X-ray beam such that only a region of interest of the imaged anatomy, such as a nodule or lump within a breast, is irradiated. This may be useful in a diagnostic mode, where a suspicious region within the breast has been identified and is being imaged but where the surrounding tissue is not of interest and need not be irradiated.

Figure 4:
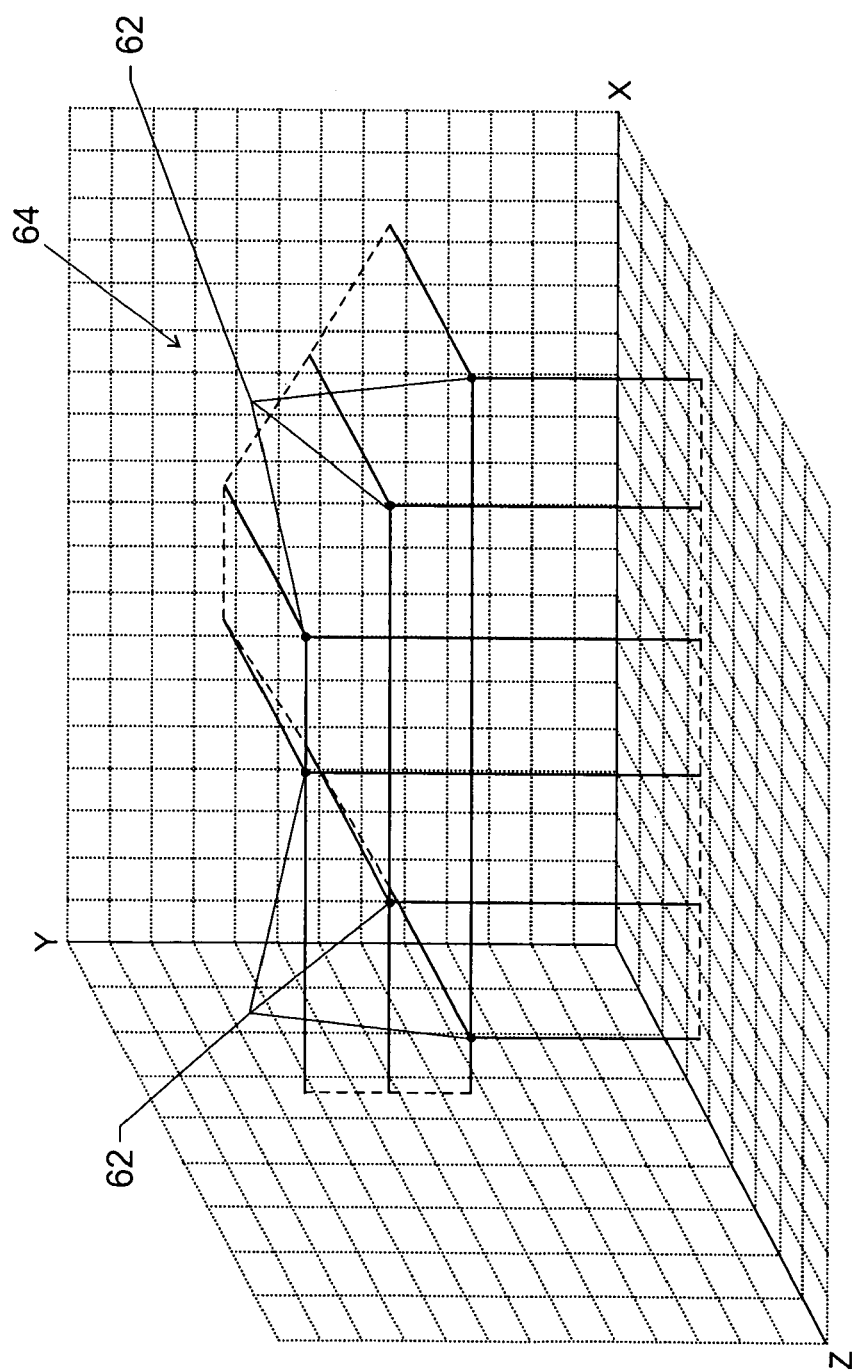
FIG. 4 depicts source positions generally along an imaging trajectory which is curved in one-dimension, in accordance with the present technique.
Figure 5:
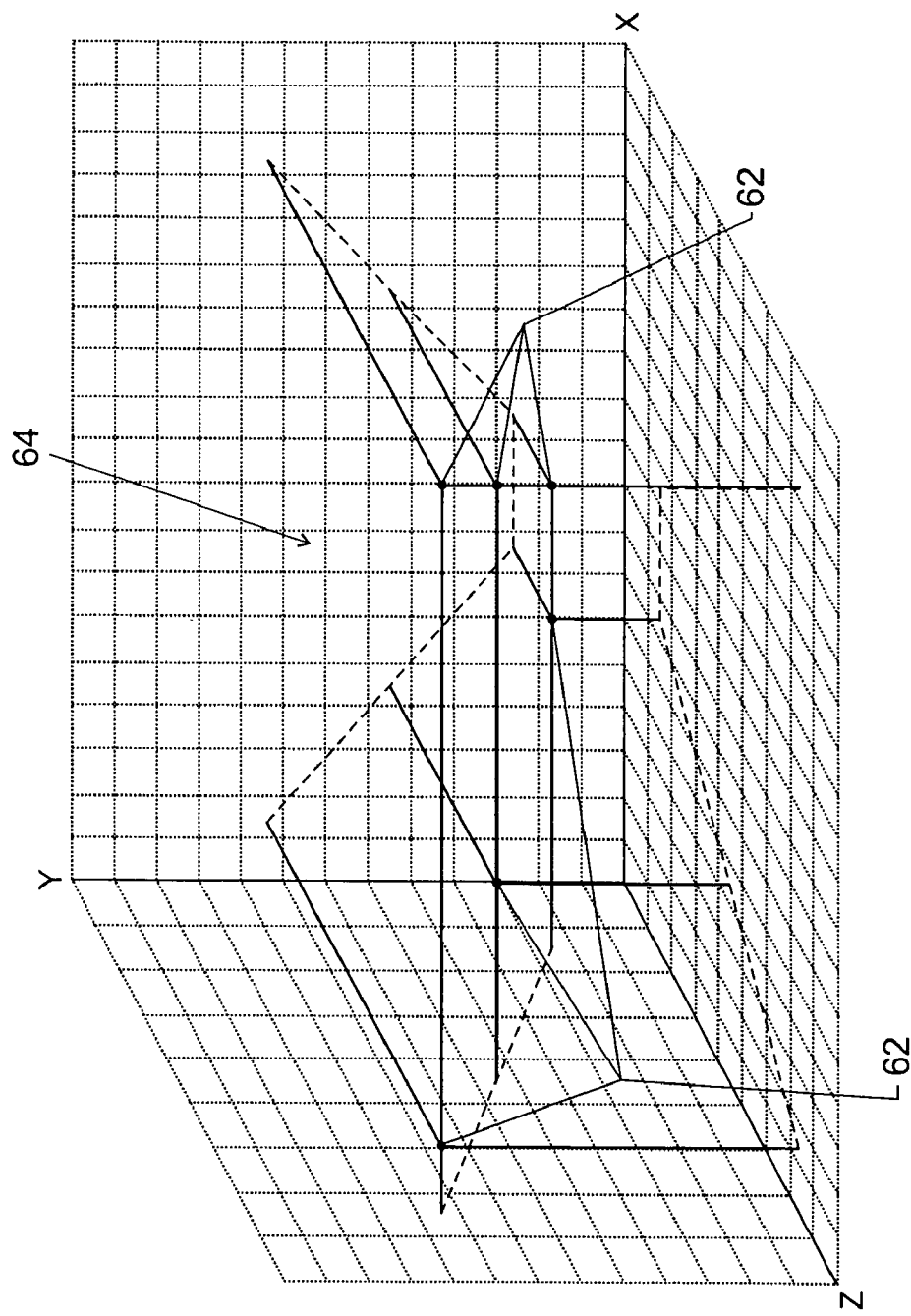
FIG. 5 depicts source positions generally along an imaging trajectory which is curved in two-dimensions, in accordance with the present technique.
Figure 6:
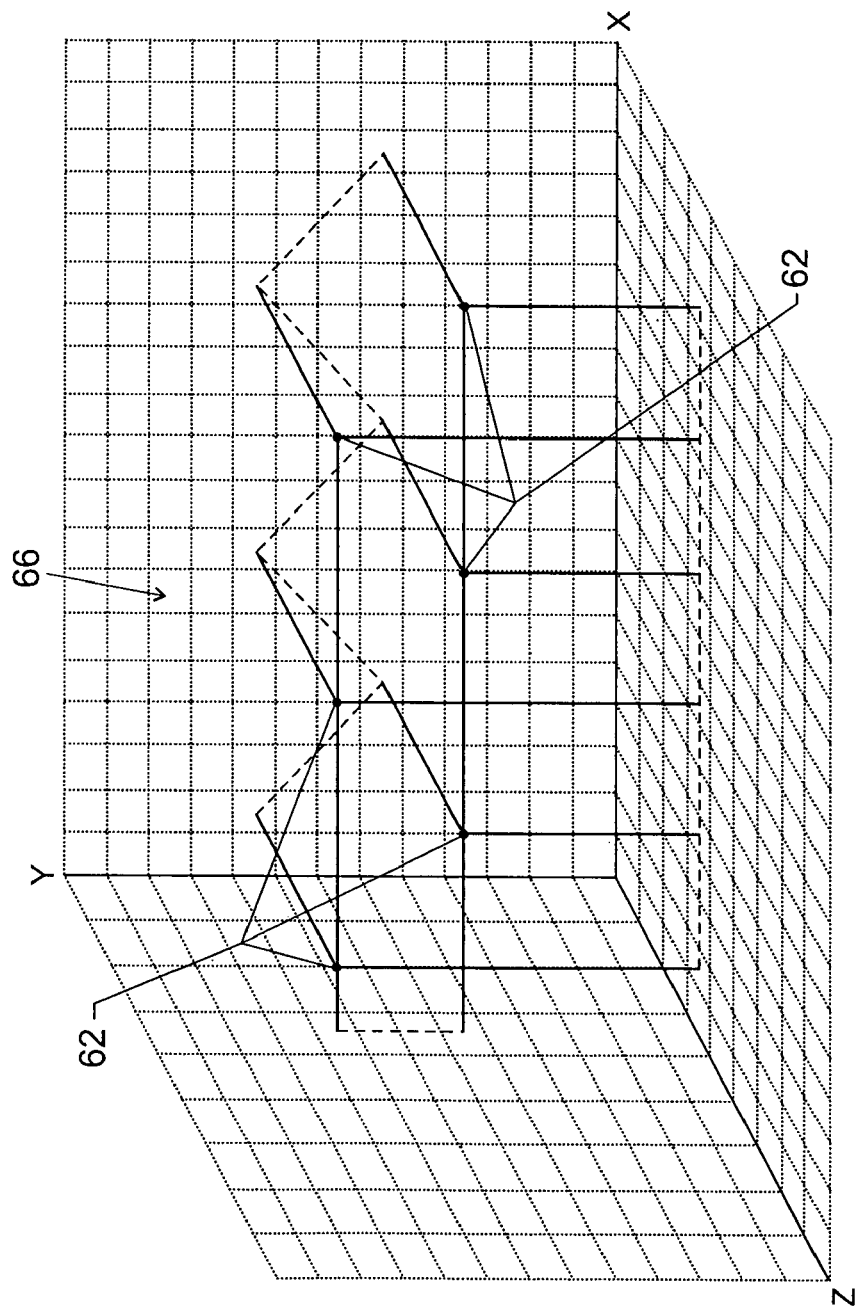
FIG. 6 depicts source positions generally along a sinusoidal imaging trajectory, in accordance with the present technique.
Figure 7:
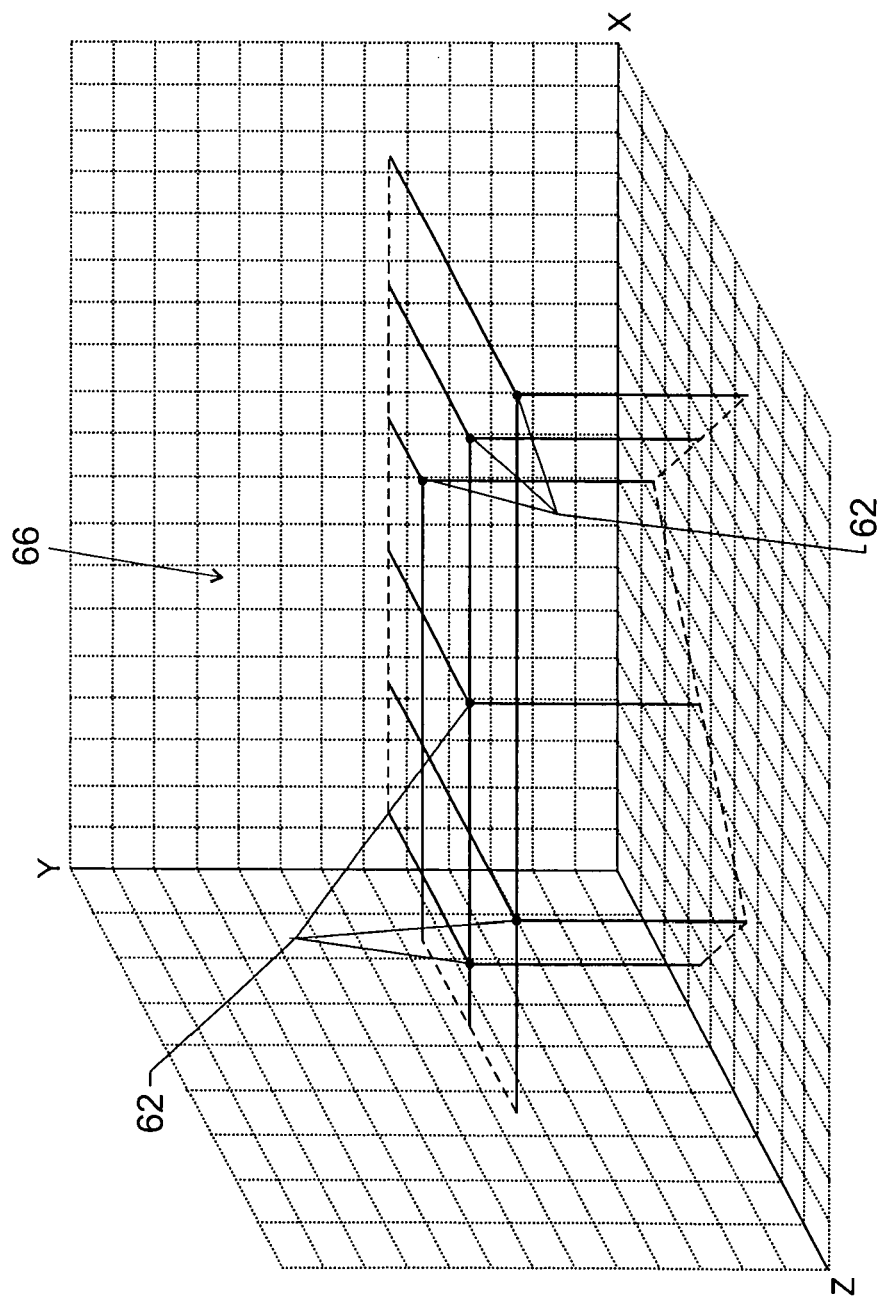
FIG. 7 depicts source positions generally along a second generally sinusoidal imaging trajectory, in accordance with the present technique.
Figure 8:
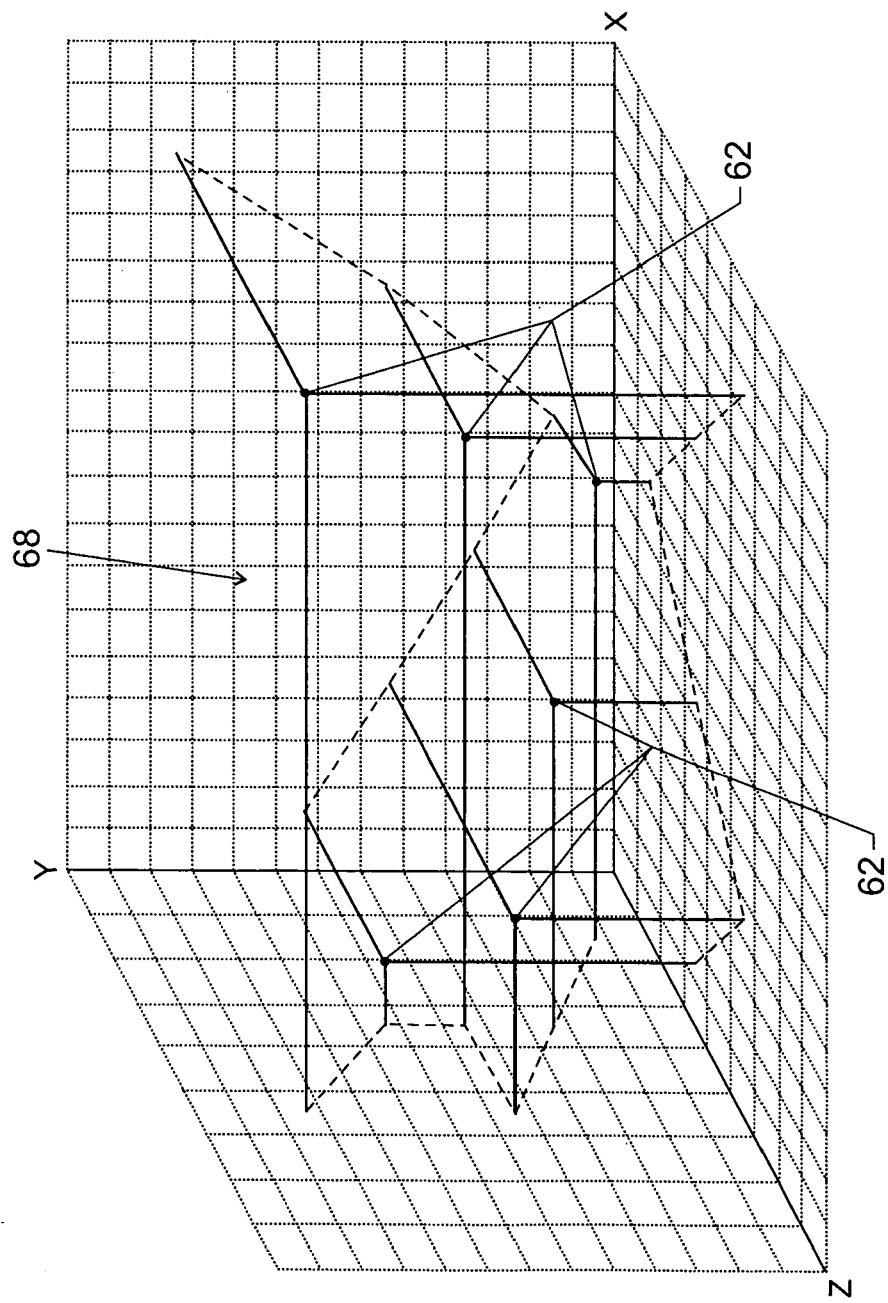
FIG. 8 depicts source positions generally along an arbitrary imaging trajectory, in accordance with the present technique.

While the linear imaging trajectory 60 is one possible trajectory, other imaging trajectories are also possible. For example, as depicted in FIG. 4, the emission points 62 may occur on a curved imaging trajectory 64. The curved imaging trajectory 64 may be oriented in virtually any direction, such as the alternative orientation of the curved imaging trajectory 64 depicts in FIG. 5. More complex trajectories may also be employed, such as a sinusoidal imaging trajectory 66, as depicted in FIGS. 6 and 7. In addition, more complex composite and or arbitrary imaging trajectories may also be employed, such as the arbitrary imaging trajectory 68 depicted in FIG. 8. Indeed, the imaging trajectory may encompass virtually any points within the three-dimensional space available to or encompassing the X-ray source 12. Also, as shown in FIG. 7, the points along the imaging trajectory do not need to be uniformly spaced. As one of ordinary skill in the art will appreciate, however, hardware constraints, i.e., mechanical setup, support, drives, and so forth, and clinical constraints may limit the three-dimensional space available to or encompassing the X-ray source 12. In general, the imaging trajectory will be determined based upon the impact of the position and timing of X-ray emissions on the final three-dimensional image quality and based upon whatever hardware and clinical constraints may be present.

While the present technique is not limited in terms of the projection angles at which projection images are acquired along a desired trajectory, projection angles that image, i.e., expose, only the breast are generally more useful for mammography. For example, a projection image acquired from the front of the patient 16 may contain image data representative of the chest and lungs as well as of the breast. Because of the potential confounding of image data associated with the breast and image data associated with non-breast tissue, the use of such projection images may be impractical. Therefore, while arbitrary tube positions may be utilized in conjunction with the present technique, in general projection images are acquired at projection angles where only the breast is imaged.

Other factors and/or variables associated with the X-ray source 12, such as target/filter combination, kVp and mAs, may be configured for the acquisition step 52. Such factors and/or variables may be determined or configured by adapting an existing standard mammography technique (which may be chosen, for example, as a function of the compressed breast thickness) to the tomosynthesis acquisition. For example, a kVp may be chosen for tomosynthesis mammography which is the same as a kVp already used in standard mammography but in which the mAs is adapted for tomosynthesis by equally distributing some fixed multiple of the mAs across the number of acquired projection images 78. In one example, 1.5 times the dose for a standard mammogram is distributed across 21 projection images. While the mAs may be equally distributed across the number of projection images 78 acquired, it may also be weighted, for example, to account for a varying pathlength through the tissue. This may be important for large projection angles, compared to the standard mammographic exam projection angle, in combination with an anisotropic shape of the imaged anatomy. For example, when imaging the compressed breast, which is non-isotropic, a higher mAs may be chosen to offset the longer pathlength through the tissue for large angles.

In addition, the kVp may also be adjusted between images. In particular, a higher kVp may provide better penetration, and thus may be desired where the pathlength through he imaged tissue is long relative to other imaging orientations. Generally, mAs and/or kVp may be determined as a function of different acquisition parameters, such as projection angle, distance between detector and tube, and so forth. For example, mAs and/or kVp may be determined according to pre-determined values, such as for a breast of a given thickness, or according to a functional relationship between breast thickness, tube and detector position, pre-shot parameters, and so forth. Similarly, the time for exposure, and therefore the mAs, may be controlled by continuously reading out an additional sensor or region of the detector 18 and stopping the exposure, i.e., X-ray emission, when a specified signal level is reached. In this manner a desired image quality for each projection image 78 may be obtained. Though desired values of mAs and kVp may be determined by modifying known mammographic configurations, as described above, they may also be determined by evaluating the image quality in a low-dose pre-shot and adjusting the technique parameters to achieve the desired image quality.

Though the preceding discussion relates to the general acquisition of image data, such as at a single energy level, the present technique may also be applied to dual energy imaging. In dual energy imaging, projection images 78 are acquired at two (or more) different energy spectra, which can then be processed, for example, to create images containing only information from a contrast medium. The high and low energy projection images can be acquired alternatingly during a single tomosynthesis scan, either for the same or for different tube positions. Alternatively, a given scan can be repeated, once with high and once with low energy spectrum.

Image Acquisition: Detector

While the above discussion generally addresses configuration and/or operation of the X-ray source 12 during acquisition step 52, configuration and operation of the detector 18 may also be a factor. In general, the detector 18 is positioned opposite the active X-ray source 12, such as the active X-ray tube or emitter, relative to the imaged anatomy. In some embodiments this may be accomplished with a single stationary detector. Alternatively, the detector 18 may be moved between X-ray exposures, such as in synchrony with a moving X-ray source 12, or to otherwise accommodate the sequence of emission points 62. Generally, if detector 18 is moved to accommodate different emission points 62, it is moved in a complementary manner such that the center of the imaged object, for the currently active emission point 62, is projected onto the center region of the detector 18. In one example, the detector 18 may be adapted to track the position of an X-ray tube, such that the detector 18 is always positioned essentially opposite of the X-ray tube with respect to the assumed center of the imaged object or the volume of interest. For example, the detector 18 may be mechanically connected to an X-ray tube, such as by a C-arm, such that movement of the X-ray tube results in a corresponding motion of the detector 18 that keeps the X-ray tube and the detector aligned relative to the center of the imaged object. When detector motion is performed in this manner, image quality may be maintained or improved, such as by reducing motion blurring due to a moving X-ray tube. For example, the motion of the detector 18 may be complementary to the motion of a moving X-ray tube with respect to the imaged anatomy. By properly adjusting the position of the detector 18, more complete image data may be acquired in spite of the limited size typically associated with detectors 18 employed in movable detector implementations.

Furthermore, the motion of the detector 18 may also incorporate angular displacement, i.e., a tilt, of the detector 18. In particular, the detector 18 may be angled or tilted differently in accordance with the imaging trajectory to keep the angle of incoming X-rays close to perpendicular at the surface of the detector 18. This is particularly beneficial in order to maintain good MTF and DQE for X-ray images that are acquired at an angle. In addition, the motion of the detector 18, angular or otherwise, may be modified by a scaling factor to account for differences in the distance between the X-ray source 12 and the imaged anatomy and between detector 18 and the imaged anatomy.

As with the X-ray source 12, the resulting trajectory and angular motion of a movable detector, whether comprising one or more than one panel, may be highly complex, and will typically be limited by the requirements in clinical practice and by the hardware configuration. However, arbitrary detector positions and/or trajectories, either during or between X-ray exposures, may be used in conjunction with the present technique.

Benefits similar to those obtained by using a moving detector or a large stationary detector, such as data completeness, may be obtained using a detector 18 consisting of multiple panels, such that a portion of the desired extent of the anatomy to be imaged is covered by at least one detector panel. In this manner, smaller, less expensive detector panels may be employed while still providing full coverage of the imaged region. Furthermore, such a multi-panel detector may consist of or include non-planar panels, depending on the hardware and/or clinical configuration. In particular, a detector 18 comprising a curved panel configured to conform to the shape of a breast may be useful in some mammography implementations. In addition, if desired, one or more panels of a multi-panel detector may be configured to move, as discussed above, such that a portion of the desired extent of the anatomy to be imaged may be covered by at least one panel of the detector 18 when the range of motion of the movable panels is taken into account. Furthermore, a steerable grid, i.e., a grid for scatter rejection that can be adjusted to the projection angle in the current projection image, may be incorporated as part of the detector 18 to reduce noise and image deterioration associated with scatter.

In some implementations a limited area detector, such as small area detectors, line detectors, or point detectors, may be employed. In such implementations, it may be advantageous to scan the limited area detector with respect to the object being imaged and for a fixed position of the X-ray source 12. In this manner, a composite image may be acquired during acquisition step 52 that corresponds to a projection image that would be acquired using a larger aperture detector. Alternately, the X-ray source 12 may move slowly and/or incrementally during a scanning process, such as a slowly moving X-ray tube, while still allowing for the generation of such a composite image. In particular, scanning of the detector 18 may be useful for mammographic imaging in order to achieve full coverage of a breast. However, even without the scanning, limited area detectors may be used to collect meaningful projection data that can be used in a three-dimensional reconstruction of the imaged anatomy.

The present technique may also benefit from using detector parameters that are optimized for low-dose tomosynthesis imaging or from differentially reading out a detector 18 or detector panel. For example, partial panel readout may occur at certain areas of the detector 18 while full resolution readout may occur at the remaining areas of detector 18. Use of optimized detector parameters and/or differential readout in this manner may improve acquisition speed and image quality.

The X-ray source 12 and the detector 18, as described above, are used to acquire projection images 78 in accordance with the present technique and as depicted at step 52 of FIG. 2. Acquisition of projection images 78 proceeds until the acquisition sequence is complete, as determined at decision block 80. For example, projection images 78 may be acquired until a specified imaging trajectory, such as a mammography imaging trajectory, is completed, i.e., until one or more projection images 78 are acquired for each emission point 62 along the specified imaging trajectory.

Reconstruction

In some instances the acquired projection images 78 may be viewed, either as acquired, i.e., raw, or after pre-processing (as described below), without being reconstructed into a three-dimensional dataset 84. For example, projections may be viewed directly, a pair of projections may be viewed in stereo, or a sequence of pairs of projections may be viewed in stereo. In such circumstances, knowledge of the system geometry during acquisition may not be required.

However, reconstruction of a three-dimensional data 84 set from the projection images 78, as depicted at step 82, generally utilizes position data 86, representative of the position of both the X-ray source 12 and the detector 18 relative to the imaged object, i.e., the acquisition geometry. Typically, to achieve good image quality, it is sufficient to know the relative geometry of the X-ray-source 12 and the detector 18. In such cases, the relative geometry may not coincide with the absolute acquisition geometry, but it will ensure that lines that connect the estimated positions of the X-ray source with the projections of any single point will intersect at a single point. However, if the absolute geometry is known, then this point of intersection is also the true location of the point, and not only will the reconstructed image quality be good, but generally the geometry of the reconstruction (e.g., distances between points, etc.) will be quantitatively correct, which may be diagnostically useful in quantifying the size of a lesion and so forth.

The position data 86, i.e., acquisition geometry, may be either pre-determined, i.e., the components of imaging system 10 are controlled to move to pre-determined locations and/or orientations, may be determined by feedback from positional sensors or feedback/readout from positioning devices associated with the components of the imaging system 10, or may be determined from the image data, such as projection images 78, using anatomical and/or fiducial markers. One of these techniques, or a combination of these techniques, may be used to determine the location and/or orientation of a moving component, such as an X-ray tube and/or the detector 18, of the imaging system 10.

The projection images 78 and the position data 86, i.e., the acquisition geometry, may be used to reconstruct a three-dimensional dataset 84 at step 82. However, other parameters and/or measurements may also be utilized during the reconstruction step 82. For example, the compressed breast thickness, which may be used to control other system parameters like maximum projection angle, volume of interest for the reconstruction, and so forth, may be a factor in the reconstruction process of step 82. Other parameters that may be of interest or specified for reconstruction include the thickness of the volume, the slice separation, one or more volumes of interest, and so forth. Such additional measurements and/or parameters may be acquired and/or provided to the reconstruction step 82 automatically or via user interaction.

The reconstruction step 82 typically employs a reconstruction algorithm, such as an algorithm based on a direct backprojection procedure. Typically the reconstruction process does not map the image data, i.e., the projection images 78, to a different geometry before reconstructing the data. However, in some cases, such a mapping may be useful. For example, in configurations where the X-ray source 12 comprises X-ray tubes disposed along a cylinder, mapping the projection images 78 to a VCT geometry may enable the use of VCT reconstruction algorithms.

The reconstruction step 82 may employ a reconstruction algorithm, such as an algorithm based on cone beam backprojection or on parallel beam backprojection. While parallel beam backprojection may not be applicable to all acquisition geometries, it allows structures at a given height above the detector 18 to be aligned by simply shifting the respective projection images 18, which may be computationally efficient. However, parallel beam backprojection generally does not account for the cone beam magnification attributable to the system.

Various reconstruction algorithms for tomosynthesis exist. These reconstruction algorithms include Filtered Backprojection (FBP), Generalized Filtered Backprojection (GFBP), Algebraic Reconstruction Technique (ART), multiplicative ART, Matrix Inversion Tomosynthesis (MITS), Direct ART (DART), Order Statistics-Based Backprojection (OSBP), Simple Backprojection, Shift-and-Add (i.e., simple backprojection in a parallel beam geometry), Fourier Based Reconstruction, Objective-Function Based Reconstruction, and Maximum Likelihood and Maximum Entropy reconstructions. As one of ordinary skill in the art will appreciate, different reconstruction algorithms may be suitable for different acquisition geometries or other acquisition conditions.

The reconstruction step 82 proceeds in accordance with a specified reconstruction geometry. The reconstruction geometry typically describes the desired volume of interest for the reconstruction as well as a slice separation for the reconstruction. The reconstruction geometry may be automatically determined based upon parameters such as the compressed breast thickness, X-ray source 12 parameters, detector 18 parameters, and so forth. For example, the reconstructed volume may be determined automatically based upon the compressed breast thickness measurement or from regions of interest identified in the projections images 78 by CAD. Similarly, slice separation may be automatically defined from the maximum projection angle. Alternatively, an operator or clinician may exercise varying degrees of control over the various aspects of the reconstruction geometry, such as by specifying a volume and or slice separation or by accepting a suggested volume and/or slice separation determined by automated routines.

The reconstruction algorithm may be configured or modified to deal with data problems or inconsistencies, such as missing data (e.g., some region of the volume to be reconstructed is not projected onto the detector 18 for some of the views) and/or shadows from high attenuation structures that are not within the volume to be reconstructed (e.g., projections of high attenuation markers that are outside the volume of interest into the projection image, or "collimator shadows", i.e., projections of the collimator, which restricts the irradiated area to the volume of interest, may be visible in the collected projection images). For example, a weighted backprojection may be adjusted to address missing data or shadow problems in the image data. The weighted backprojection may also minimize out-of-plane artifacts by associating a low (or zero) weight with the corresponding regions of the image. Other approaches may also be employed during the reconstruction step 82 to improve the reconstructed image quality, including incorporating constraints into the reconstruction algorithm. For example, the reconstructed three-dimensional dataset 84 may be restricted to only physically meaningful values, to certain values or to intervals or ranges of values. Where suitable, the reconstruction algorithm employed at reconstruction step 82 may be applied to quantitative projection images, which may be generated at the pre-processing step 92, to create a quantitatively accurate three-dimensional dataset 84 representative of the imaged breast. The image quality in some reconstruction approaches may also be improved by an additional filtering step performed as part of the reconstruction step 82 or as part of a pre- or processing step 92 or post-processing step 94.

The reconstructed volume, i.e., the three-dimensional dataset 84, is typically arranged in uniformly-spaced, parallel slices, where each slice is generally parallel to the detector plane (or an approximation thereof). However, the reconstructed volume can also be arranged in other geometries, which may depend on the acquisition geometry (not just the detector orientation), the imaged anatomy or pathology, etc. In particular, non-cartesian coordinate systems (even curved) and non-uniform spacing between samples may be used.

Visualization

Once the three-dimensional dataset 84 is reconstructed, one or more visualization techniques may be employed to visualize and display desired volumes within the three-dimensional dataset 84, as depicted at step 88. The reconstructed three-dimensional datasets 84 are typically arranged in slices, which may be visualized at step 88 by slice-by-slice viewing (e.g., in a cine-loop configuration). Slice-by-slice viewing, however, may be slow (depending on the number of slices) and may convey the three-dimensional information in a less intuitive manner than desired.

Alternatively, the visualization step 88 may encompass three-dimensional visualization approaches such as maximum intensity projection (MIP), composite ray-casting (CRC), mean (or X-ray) projection, and generalized three-dimensional visualization methods. The parameters that control the appearance of the three-dimensional visualized image (e.g., transfer functions, penetration depth, etc.) may be pre-defined, may be chosen by the user, may be determined by some parameter of the imaged volume, such as the compressed thickness, or may be based on one or more statistics of the three-dimensional dataset 84. In general, three-dimensional visualization approaches may also allow operator control of properties of the visualization algorithms beyond what was available using traditional visualization methods. For example, input may be allowed for adjusting penetration depth and/or for providing contrast of the structures within the volume as a function of their respective depth.

Regardless of whether a slice-by-slice or three-dimensional visualization technique is employed, the volume to be visualized and the viewing direction may be specified by an operator and/or automated routine. For example, a volume of interest to be visualized and displayed at step 88 may be determined by an operator or clinician or may be determined by a CAD algorithm acting on the projections images 78 and/or the three-dimensional dataset 88, as discussed in greater detail below. The volume of interest may include a single slice or a set of individual slices and may include subvolumes, e.g., consisting of selected regions of slices. The volume of interest may encompass up to the entire imaged volume. The volume of interest may be viewed from the front (i.e., from the side corresponding to the X-ray source 12) and/or from the back (i.e., from the side corresponding to the detector 18).

Regardless of the selected visualization algorithm, volume of interest, and viewing direction implemented at step 88, a technique for navigating through the three-dimensional dataset 84 by modifying the viewpoint and/or the viewed volume of interest may also be provided during visualization and display step 88. Possible navigation techniques include a tumble view, which is a sequence of views from a typically circular or elliptical viewpoint trajectory, where every viewpoint is offset from the viewpoint corresponding to the projection geometry for some central projection by some fixed angle. Such a tumble view technique may be combined with a varying depth of the viewpoint. In addition, though circular tumble view trajectories are generally employed, other two and three-dimensional trajectories may also be employed. For example, the maximum view angle of the viewpoint trajectory in any one direction may be determined based on the acquisition geometry. Using a viewpoint trajectory based on acquisition geometry in this manner may allow the visual impact of the non-isotropic resolution, which is typical in tomosynthesis, to be reduced or minimized.

The visualization and display step 88 may also incorporate additional image data 90, such as image data acquired at different times or by different modalities. The additional image data 90 may be co-registered with the three-dimensional dataset 84 if the acquisitions are contemporaneous. Alternatively, the additional image data 90 may be acquired independently of the acquisition of the tomosynthesis mammography image data. If the additional image data 90 is acquired independently, a suitable algorithm may be employed to register the datasets, such as in a pre- or post-processing step, as described below.

In instances where the additional image data 90 is acquired at different times, such as during a previous mammogram or tomosynthesis mammogram, changes over time may be visualized and displayed at step 88. For instance, the present technique may be used to track changes within an imaged breast, by suitably correlating the current projections images 78 and/or three-dimensional dataset 84 with earlier projection images 78 and/or three-dimensional datasets 84, such as a previous mammogram or tomosynthesis mammogram. For example, a previous three-dimensional dataset 84 may be normalized and registered with a current three-dimensional dataset 84, using a suitable registration algorithm. The two three-dimensional datasets 84 may then be subtracted from each other and the difference image visualized and displayed at step 88, thereby emphasizing regions and structures within the breast where a change has occurred in the intervening time period.

The additional image data 90 may also include image data derived via other imaging modalities. These modalities include, but are not limited to, ultrasound, magnetic resonance imaging (MRI), positron emission tomography (PET), nuclear imaging, thermal imaging, light imaging, and electrical impedance tomography. A registration algorithm may be applied to match the geometry of the two or more image datasets if the image datasets are not co-registered, i.e., acquired without changing the position of the imaged breast. For example, a three-dimensional dataset 84 and an ultrasound dataset may be acquired in co-registered fashion and would not need to be registered by application of a registration algorithm. However, even in this situation, a registration algorithm may be applied to improve the registration between the datasets.

Since different imaging modalities not only show different properties of the imaged tissue, but may also exhibit different imaging characteristics (e.g., resolution), the dataset from one modality may be used to improve the reconstruction in another modality. For instance, in the ultrasound example, the co-registered ultrasound dataset may exhibit a z-resolution of about 0.1 mm, which may be used to improve the reconstruction quality of the three-dimensional dataset 84, which may have an inherent depth, or z-resolution, of about 0.5 mm. The visualized and displayed three-dimensional datasets 84, alone or in conjunction with images acquired by other modalities, may be used for diagnosis, for routine monitoring and examination, for treatment tracking (e.g., quantify the size of a lesion, and follow that lesion in subsequent exams to evaluate the efficacy of a given treatment), and/or for interventional procedures (surgical planning, generalized stereotaxy, etc.)

Pre-Processing

While the preceding discussion relates generally to tomosynthesis mammography, additional processing may be performed at various points to facilitate the technique. For example, a pre-processing step may be performed on some or all of the projection images 78 prior to the reconstruction step 82. For example, the pre-processing step 92 may include combining projection images 78 from different detector positions/regions into a single image that can then be used for further processing. Such a combination may be performed when the detector 18 is a small area, line, or point detector that is scanned while the X-ray source 12 is stationary.

The pre-processing step 82 may also compensate for different imaging effects to facilitate reconstruction of the projection images 78. For example, the pre-processing step 92 may correct the pixel values of the projection images 78 to correspond to the average linear attenuation value (for some reference energy, or energy spectrum) along the path of the corresponding ray through the tissue. Similarly, the pixel values of the projection images 78 may be processed to indicate the tissue composition along the ray-path.

The pre-processing step 92 may include offset, gain and bad-pixel corrections, as well as corrections for geometry effects due to differences in the distance between the detector 18 and the X-ray source 12, differences in the incident angle, and/or differences in the pathlength through imaged volume and/or tissue. In addition, the pre-processing step 92 may include taking the negative log and/or compensating for different imaging techniques or configurations, such as compensation based on mAs and/or kVp, either from the used acquisition parameters or estimated from the data, i.e., projection images 78. The pre-processing step may also perform scatter correction, based on compressed thickness and/or other parameters, and/or deconvolution of the image data, such as to reduce motion or vibration blurring, MTF effects, and so forth.

The pre-processing step 92 may also include processing techniques for thickness compensation, dynamic range management (DRM), findings-based filtration (FBF), and so forth, which may be useful for displaying the projection images 78 to a clinician or for preparing the projection images 78 for subsequent processing. In addition, the pre-processing step 92 may include functions such as segmenting regions of the projection images 78, such as background or regions of interest, including shadows of markers, collimator boundaries, and so forth. Modification or differential processing of segmented regions, such as differential adjustment of intensity values, may occur during the pre-processing step 92 to facilitate image review and/or further processing. Similarly, fiducial and/or anatomical markers may be identified and used to identify the relative or absolute system geometry during the pre-processing step 92. Segmentation of markers or other regions may be performed automatically, such as using threshold based techniques, or may be performed using input from a clinician. Clinician input may range from actual selection of the segmented regions to acceptance or modification of segmented regions suggested by an automated routine.

Post-Processing

A post-processing step 94 may also be performed, such as on the reconstructed three-dimensional dataset 84. The post-processing step 94 may generally be directed to improving the image quality in the three-dimensional dataset 84 or to prepare the three-dimensional dataset 84 for subsequent processing steps. For example, the post-processing step 94 may geometrically reformat the three-dimensional dataset 84 to conform to a rectangular grid, if parallel projection geometry was used in the reconstruction step 82, ensuring correct size and/or distance measurements. Geometric reformatting may also allow for interpolation of the three-dimensional dataset 84 to provide isotropic voxel size, which may be useful in a subsequent visualization step 88.

The post-processing step 94 may also remove artifacts as well as deconvolute or deblur the image data to reduce blurring due to motion or vibration. In addition, the post-processing step 94 may include thickness compensation, dynamic range management (DRM), findings-based filtration (FBF), histogram equalization, and/or other image enhancement algorithms. The post-processing step 94 may also segment regions of the image, such as anatomical structure, background and/or reconstructions of markers, and modify the image data within these regions, such as by adjusting intensity values. While the post-processing step 94 may be useful in preparing the three-dimensional dataset 84 for display, the post-processing step 94 may also prepare the three-dimensional dataset 84 for further processing.

As may be noted in the preceding discussion, there may be overlap in the type of image processing and/or modifications that can be performed at a pre-processing step 92 or at a post-processing step 94. To the extent that a similar result can be achieved by either a pre-processing or a post-processing step implementation, the computationally less intensive alternative is typically chosen.

CAD Processing

In addition to human evaluators, automated routines may also be employed to evaluate medical image data, either in the form of projection images 78 and/or three-dimensional dataset 84. In particular, the projection images 78 and/or the three-dimensional dataset 84 may be analyzed by computer-implemented routines to identify regions of interest (Computer Aided Detection) or to make a diagnosis (Computer Aided Diagnosis). The acronym CAD typically refers to either of these functions.

CAD processing of this type may be included in the present technique, such as via one or more CAD processing step 96. Depending on the purpose and nature of the CAD processing steps 96 to be implemented, CAD processing steps 96 may be performed prior to and/or subsequent to the reconstruction step 84. For example, a CAD algorithm may define regions of interest (ROI) in the projection images 78, which can be used to define a volume of interest (VOI) for the reconstruction step 84. Alternatively, CAD processing may include the derivation of general risk metrics, such as from tissue decomposition performed on the three-dimensional dataset 84.

With regard to a CAD processing step 96 implemented fully or partially prior to the reconstruction step 82, the projection images 78 from different acquisition positions can be analyzed directly. The CAD algorithm may analyze the projection images 78 individually, in pairs (stereo), or as a full projection set, where correlations between the images can be used in the analysis. Furthermore, a CAD processing step 96 occurring prior to the reconstruction step 82 may be employed in conjunction with a pre-processing step 92 if desired. For example, a pre-processing step 92 may be performed to provide feature enhancement and/or artifact suppression prior to analysis by the CAD processing step 96. Similarly, a pre-processing step 92 that processes the projection images 78 based on the acquisition orientation relative to the imaged anatomy may also be performed prior to analysis by the CAD processing step 96 to reduce orientation dependent variability prior to CAD analysis. Other system characteristics may also be accounted for, either by a pre-processing step 92 or by the CAD processing step 96 itself. For example, the projection images 78 may be processed to account for spatial resolution, noise characteristics, and other parameters, either via the pre-processing step 92 or the CAD processing step 96.

With regard to a CAD processing step implemented fully or partially subsequent to the reconstruction step 82, the CAD analysis may be done slice-by-slice using individual two-dimensional images (slices) or multiple two-dimensional images. Alternatively, and concurrently, reprojected images created from the full volume or from subvolumes may be used. For example, thick slices, which are essentially reprojections (or average images) of small sets of adjacent slices may be analyzed at the CAD processing step 96. Alternately, the analysis can be done using the full three-dimensional dataset 84. Since the full three-dimensional dataset 84 is not subject to many of the problems of feature superposition that are present in the projection images 78, it may generally be preferable to process the three-dimensional dataset 84 using CAD algorithms.

The CAD algorithm employed may generate results based on the specified image data as well as other patient specific data, such as patient risk factors. These patient risk factors may include patient age, health history, lifestyle, family history, etc. In addition, genomic risk factors such as presence of BRCA1/BRCA2, HER-2, and other risk-related alleles may also be taken into account. Furthermore, image based risk metrics, such as % fibroglandular tissue, may be correlated to risk. The more accurate assessment of % fibroglandular tissue, together with the improved assessment of the three-dimensional distribution of fibroglandular tissue within the breast, available from quantitative three-dimensional images may, therefore, improve performance of a CAD algorithm employed at the CAD processing step 96.

As one might expect, since the operation of a CAD algorithm is unrelated to the operation of the human visual system, processing image data for a CAD analysis may be different than processing image data for display to an operator or reviewer. In particular, the algorithms, parameters, and/or routines associated with a pre-processing step 92, a reconstruction step 82, and/or a post-processing step 94 may all be adjusted to facilitate the operation of a CAD processing step 96. As a result, processing of the projection images 78 and/or of the three-dimensional dataset 84 for CAD analysis may be performed instead of or in addition to processing intended to improve the visual display of images for a viewer. As one of ordinary skill in the art will appreciate, however, the results of a CAD analysis may be incorporated into the visualized and displayed images at step 88 so that a clinician may evaluate and/or review the results of the CAD analysis in conjunction with the displayed image data.

EXAMPLE

An exemplary implementation of the foregoing technique is now presented. In this exemplary implementation a three-dimensional imaging system 10 acquires twenty-one projections over a 60° angular range in approximately eight seconds. The X-ray source 12 includes an X-ray tube which moves in a trajectory above the detector 22 and stationary breast. The Source to Image Distance (SID) is 660 mm. For a relatively thick, dense breast (such as 6 cm of compressed thickness), a technique of Rh/Rh at 30 kVp and 160 mAs total may be used. The mAs per tomosynthesis view is $160/21 = 7.62$ mAs. The X-ray tube current is approximately 75 mA, for an X-ray "on" time per shot of approximately 0.1 sec. Both the X-ray tube and the detector 22 move during each X-ray exposure. In this example, the X-ray tube moves by approximately 240 microns and the detector 22 moves by approximately 20 microns. The X-ray tube also moves between exposures. Total dose for the tomosynthesis mammogram is approximately 1.5 times the dose used in a single conventional mammogram in this example. In general the view dose may range from 1 to 3 times the standard view dose, though doses between 0.5 to 10 times the standard view dose may be employed.

A pre-shot for the automatic optimization of parameters (AOP) may be performed at a tube angle of 0°, and exposure parameters for the projection sequence may be calculated while the X-ray tube moves to the + or −30° position for a first acquisition in the sequence. The first, eleventh, and twenty-first images in the sequence may be displayed at reduced resolution after the exam as a quality control measure. In this example, the first image is displayed no later than 5 seconds after the end of the final X-ray exposure, with the eleventh and twenty-first images following in 1 second increments or less.

In this example, the detector 22 captures 1920×2304 pixels at 100 micron resolution. As one of ordinary skill in the art will appreciate, larger detectors may also be employed. Fourteen bits of information are encoded per pixel in a two byte data word. Each projection image is approximately 8.8 Mbytes in size, and the twenty-one image sequence is approximately 177 Mbytes in size. Data transfer time to a reconstruction workstation 28 or display workstation 30 is approximately 22 seconds or less. Detector parameters are optimized for low dose tomosynthesis imaging.

Projection images 78 are reconstructed into three-dimensional datasets 84 having a typical size of 1920×2304×90 for a 4.5 cm compressed breast. That is, the x,y resolution is approximately 100 microns, and the z (depth) resolution is approximately 0.5 mm. Slices can be reconstructed at any z-spacing (larger or smaller than 0.5 mm). Reconstruction may be completed in approximately 5 seconds. Images may be reviewed in cine mode, with display rates of up to 15 frames per second or more. The generalized filtered backprojection reconstruction algorithm is used for reconstruction.

Image review may also be done in a volume rendering mode. In an example of this mode, the first image displayed is a standard mammogram calculated from the three-dimensional dataset 84. Mean intensity projection, maximum intensity projection, or composite ray casting can be used for the calculation. This initial view may provide anatomical context for a radiologist or technologist. Thick slices, computed with the same algorithms, may be displayed to help focus on specific regions of the anatomy. Tumble views may then be presented in a standard volume rendering format. That is, the viewing angle "tumbles" around the X-ray beam direction incident on the anatomy. The range of viewing angles is typically +/−5° in the azimuthal direction (perpendicular to the scanning direction) and +/−15° to +/−30° in the elevation scanning direction (parallel to the scanning direction). Images may be reviewed with display rates of 15 frames per second or less.

Conclusion

The 3D imaging method according to the present invention is extremely flexible, and can also be used for imaging larger areas than one would normally image with a detector of the given size. For example, with the methods outlined above it is straightforward to perform a full body imaging, by moving the x-ray source and the detector with respect to the patient in such a way that every region of the body is viewed from at least two projection angles. In one embodiment, the 3D imaging system of the present invention can replace a CT system in the ER.

Furthermore, as noted above, the imaging chain described herein may vary in terms of the steps performed and/or the order in which they are performed. In general, processing can be applied at any stage of the imaging chain, such as to enhance certain features in the images, to reduce artifacts, to provide corrections to the data for image chain deficiencies, or to calibrate the system 10. Generally, any such processing step maps the image data into a more desirable form, for example by improving conspicuity of anatomical features (e.g., lesions), facilitating direct interpretation of certain properties of the imaged anatomy (e.g., in tissue decomposition), or by enabling subsequent processing steps (e.g., 3D reconstruction).

A tomosynthesis mammography system as described herein may be used in mammography screening, diagnostic imaging, or interventional imaging. Because the tomosynthesis mammograms provide three-dimensional information about the breast, the mechanical compression typically associated with mammography can be reduced or eliminated. Similarly, the dose used for the individual X-ray images may be reduced compared to standard mammography, since multiple images are used for interpretation. In particular, the total X-ray dose from the multiple acquired views may be comparable to the dose used for a standard mammogram.

While the invention may be susceptible to various modifications and alternative forms, specific embodiments have been shown by way of example in the drawings and have been described in detail herein. However, it should be understood that the invention is not intended to be limited to the particular forms disclosed. For example, the present techniques may be generally applicable to other medical and non-medical imaging contexts, such as security screening, i.e., baggage, package, and/or passenger screening. Indeed, the invention is to cover all modifications, equivalents, and alternatives falling within the spirit and scope of the invention as defined by the following appended claims.

What is claimed is:

1. A method for generating a three-dimensional dataset, the method comprising the acts of:
   acquiring a plurality of projection images from different locations on an arbitrary imaging trajectory; and
   reconstructing the plurality of projection images to form a three-dimensional dataset.

2. The method as recited in claim 1, comprising the act of:
   visualizing a selected volume of the three-dimensional dataset.

3. The method as recited in claim 1, comprising the act of:
   processing at least one of the plurality of projection images, the three dimensional dataset, and a volume subset of the three-dimensional dataset using a CAD algorithm.

4. The method as recited in claim 1, comprising the act of:
   processing at least one of the plurality of projection images, the three dimensional dataset, and a volume subset of the three-dimensional dataset prior to processing by a CAD algorithm or to visualization.

5. The method as recited in claim 1, wherein acquiring the plurality of projection images comprises:
   emitting X-rays from one or more X-ray sources at a plurality of locations on the arbitrary imaging trajectory; and
   generating at least one projection image corresponding to each location from which X-rays are emitted.

6. The method as recited in claim 1, wherein acquiring the plurality of projection images comprises:
   moving an X-ray source along the arbitrary imaging trajectory;
   emitting X-rays from the X-ray source at a plurality of locations on the arbitrary imaging trajectory; and
   generating at least one projection image corresponding to each location from which X-rays are emitted.

7. The method as recited in claim 1, wherein acquiring the plurality of projection images comprises:
   emitting X-rays from a plurality of X-ray sources, wherein each X-ray source may be positioned at one or more locations on the arbitrary imaging trajectory and wherein only one X-ray source is active at a time; and
   generating at least one projection image corresponding to each location from which X-rays are emitted.

8. The method as recited in claim 7, wherein each X-ray source is stationary.

9. The method as recited in claim 1, wherein the three-dimensional dataset comprises mammography image data.

10. A tangible, machine readable media, comprising:
    code adapted to control acquisition of a plurality of projection images from different locations on an arbitrary imaging trajectory; and
    code adapted to reconstruct the plurality of projection images to form a three-dimensional dataset.

11. The tangible, machine readable media, as recited in claim 10, comprising:
    code adapted to visualize a selected volume of the three-dimensional dataset.

12. The tangible, machine readable media, as recited in claim 10, comprising:
   code adapted to process at least one of the plurality of projection images, the three dimensional dataset, and a volume subset of the three-dimensional dataset using a CAD algorithm.

13. The tangible, machine readable media, as recited in claim 10, comprising:
   code adapted to process at least one of the plurality of projection images, the three dimensional dataset, and a volume subset of the three-dimensional dataset prior to processing by a CAD algorithm or to visualization.

14. The tangible, machine readable media, as recited in claim 10, comprising code adapted to control emission of X-rays from one or more X-ray sources at a plurality of locations on the arbitrary imaging trajectory.

15. The tangible, machine readable media, as recited in claim 10, wherein the code adapted to acquire the plurality of projection images moves an X-ray source along the arbitrary imaging trajectory, emits X-rays from the X-ray source at a plurality of locations on the arbitrary imaging trajectory, and generates at least one projection image corresponding to each location from which X-rays are emitted.

16. The tangible, machine readable media, as recited in claim 10, wherein the code adapted to acquire the plurality of projection images emits X-rays from a plurality of X-ray sources, wherein each X-ray source may be positioned at one or more locations on the arbitrary imaging trajectory and wherein only one X-ray source is active at a time, and generates at least one projection image corresponding to each location from which X-rays are emitted.

17. An imaging system, comprising:
   means for acquiring a plurality of projection images from different locations on an arbitrary imaging trajectory; and
   means for reconstructing the plurality of projection images to form a three-dimensional dataset.

18. An imaging system, comprising:
   an X-ray source configured to move along an arbitrary imaging trajectory;
   a positioner configured to move at least the X-ray source;
   a system controller configured to operate the X-ray source;
   a detector configured to detect X-rays emitted by the X-ray source at different locations on the arbitrary imaging trajectory and to generate signals in response to the detected X-rays; and
   a detector interface configured to acquire the signals from the detector.

19. The imaging system, as recited in claim 18, comprising:
   a reconstruction workstation configured to reconstruct image data from the signals acquired by the detector interface.

20. The imaging system, as recited in claim 18, comprising:
   a review workstation configured to display images reconstructed from the signals acquired by the detector interface.

21. The imaging system, as recited in claim 18, comprising:
   a picture archiving system configured to store data from at least one of the system controller, a reconstruction workstation, and a review workstation.

22. An imaging system, comprising:
   a plurality of X-ray sources, wherein each X-ray source is located at different location on an arbitrary imaging trajectory and wherein each X-ray source is individually activated;
   a system controller configured to operate the plurality of X-ray sources;
   a detector configured to detect X-rays emitted by each respective X-ray source and to generate signals in response to the detected X-rays; and
   a detector interface configured to acquire the signals from the detector.

23. The imaging system, as recited in claim 22, comprising:
   a reconstruction workstation configured to reconstruct image data from the signals acquired by the detector interface.

24. The imaging system, as recited in claim 22, comprising:
   a review workstation configured to display images reconstructed from the signals acquired by the detector interface.

25. The imaging system, as recited in claim 22, comprising:
   a picture archiving system configured to store data from at least one of the system controller, a reconstruction workstation, and a review workstation.

* * * * *